US012605285B2

(12) United States Patent
Moloney

(10) Patent No.: US 12,605,285 B2
(45) Date of Patent: Apr. 21, 2026

(54) WOUND DRESSING

(71) Applicant: HIDRAMED SOLUTIONS LTD, Dublin (IE)

(72) Inventor: Suzanne Marie Moloney, Dublin (IE)

(73) Assignee: HIDRAMED SOLUTIONS LTD, Dublin (IE)

( * ) Notice: Subject to any disclaimer, the term of this patent is extended or adjusted under 35 U.S.C. 154(b) by 850 days.

(21) Appl. No.: 16/637,989

(22) PCT Filed: Jul. 20, 2018

(86) PCT No.: PCT/EP2018/069842
§ 371 (c)(1),
(2) Date: Feb. 10, 2020

(87) PCT Pub. No.: WO2019/029978
PCT Pub. Date: Feb. 14, 2019

(65) Prior Publication Data
US 2020/0237561 A1 Jul. 30, 2020

(30) Foreign Application Priority Data

Aug. 11, 2017 (IE) .................................... S2017/0161

(51) Int. Cl.
*A61F 13/00* (2024.01)
*A61F 13/15* (2006.01)

(52) U.S. Cl.
CPC .................... *A61F 13/00051* (2013.01); *A61F 2013/00093* (2013.01); *A61F 2013/15186* (2013.01)

(58) Field of Classification Search
CPC .... A61F 13/00051; A61F 13/10; A61F 13/14; A61F 13/061; A61F 13/64; A61F 13/505; A61F 2013/00093; A61F 2013/15186

(Continued)

(56) References Cited

U.S. PATENT DOCUMENTS 4,732,146 A * 3/1988 Fasline ............... A61F 13/0269
602/79
5,456,660 A 10/1995 Reich et al.
(Continued)

FOREIGN PATENT DOCUMENTS

CN 103370036 A 10/2013
CN 204798132 U 11/2015
(Continued)

OTHER PUBLICATIONS

Spacer Fabric, Science Direct, 2023, p. 1. [online], [retrieved on Dec. 10, 2023]. Retrieved from the Internet<URL: https://www.sciencedirect.com/topics/engineering/spacer-fabric#:~:text=Spacer%20fabrics%20are%20a%20kind,from%201.5%20to%2010%20mm. (Year: 2023).*

(Continued)

*Primary Examiner* — Alireza Nia
*Assistant Examiner* — Gina McCarthy
(74) *Attorney, Agent, or Firm* — DLA Piper LLP (US)

(57) ABSTRACT

The invention relates to a wound dressing device for securing a dressing in position on a wound, wherein the wound dressing device comprises: a retaining device for encompassing a portion of the body; a dressing, and; a fastening element that can secure the dressing in position. The fastening element being configured at least substantially external to the retaining device, the dressing being configured at least substantially internal to the retaining device, such that the dressing can be secured to the fastening element through the retaining device. The invention also relates to a method of applying the device and to a combined dressing and fastening element.

21 Claims, 4 Drawing Sheets

Figures 3, 8:
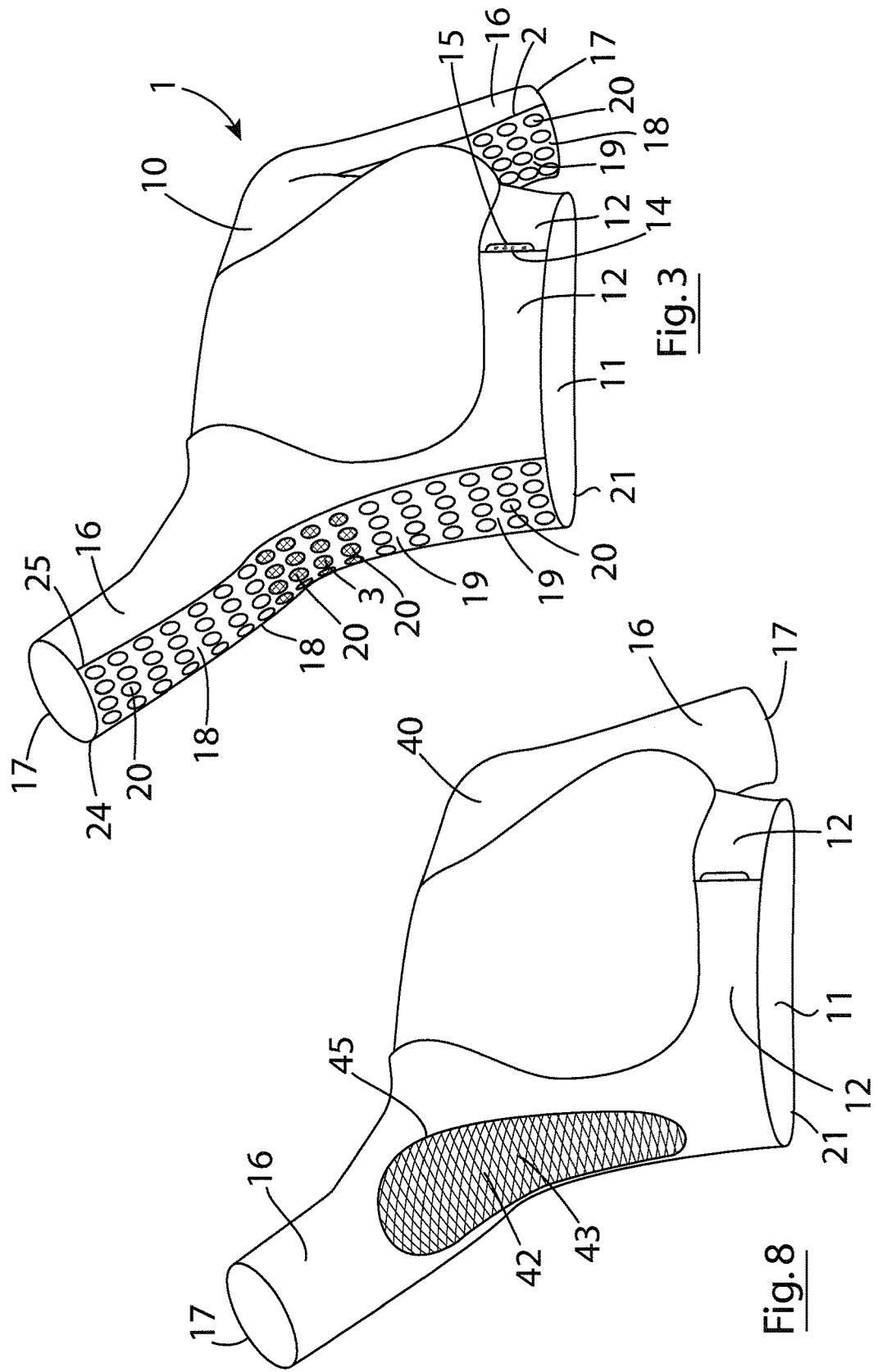

(58) Field of Classification Search
USPC .............................................. 602/79; 24/441
See application file for complete search history.

(56) References Cited

U.S. PATENT DOCUMENTS

| | | | |
|---|---|---|---|
| 5,538,500 A | | 7/1996 | Peterson |
| 5,609,569 A | | 3/1997 | Offenhartz |
| 5,662,599 A | * | 9/1997 | Reich .................... A61F 13/146 602/59 |
| 6,399,852 B1 | * | 6/2002 | Barron ................ A61F 13/0269 602/41 |
| 6,548,728 B1 | | 4/2003 | Faries, Jr. et al. |
| 6,659,970 B1 | * | 12/2003 | Woodworth .......... A61F 15/006 602/42 |
| 6,932,785 B1 | | 8/2005 | Shesol |
| 7,118,545 B2 | * | 10/2006 | Boyde ................. A61F 13/0226 602/53 |
| 9,003,615 B1 | * | 4/2015 | Cates, Jr. ........... A44B 18/0003 24/442 |
| 9,433,544 B1 | | 9/2016 | Ross |
| 9,795,516 B2 | | 10/2017 | Cureton et al. |
| 9,943,452 B1 | * | 4/2018 | Sundheimer .......... A61F 13/622 |
| 2010/0082007 A1 | | 4/2010 | Bobo |
| 2011/0319798 A1 | * | 12/2011 | DiGrazia .............. A61F 15/004 602/54 |
| 2016/0151211 A1 | | 6/2016 | Biddlestone |
| 2016/0346565 A1 | | 12/2016 | Rhodes et al. |
| 2017/0100300 A1 | * | 4/2017 | Rapp ................... A61B 5/6824 |
| 2019/0216653 A1 | * | 7/2019 | Ganzoni ................... A61F 5/32 |

FOREIGN PATENT DOCUMENTS

| | | | |
|---|---|---|---|
| EP | 2765957 A1 | 8/2014 | |
| GB | 2439525 A | 1/2008 | |
| KR | 101261840 B1 | 5/2013 | |
| WO | 1997006761 A1 | 2/1997 | |
| WO | 2013055892 A1 | 4/2013 | |
| WO | 2015022334 A1 | 2/2015 | |

OTHER PUBLICATIONS

Notice of Reasons for Refusal (Final Official Action) dated Jan. 10, 2023 on corresponding Japanese application 2020-529812 (English translation included).

First Office Action for CN 201880050259.1 dated Aug. 5, 2021.

Second Office Action for CN 201880050259.1 dated Feb. 7, 2022.

International Search Report for PCT Application No. PCT/EP2018/069842 dated Oct. 4, 2018.

European Examination Report for EP 18745565.4 dated Jan. 17, 2020.

European Office Action for EP 18745565 dated Mar. 30, 2020.

European Office Action for EP 18745565 dated Dec. 3, 2020.

Decision of Rejection for CN 201880060259.1 with English Translation dated Jul. 1, 2022.

Japanese Office Action for JP 2020-529812 with English Translation dated Jun. 13, 2022.

Australian Examination Report No. 1 dated Jun. 29, 2023 for corresponding Australian Patent Application No. 2018314385 (4 pages total).

European Search Report dated Oct. 17, 2022, on corresponding European Divisional Application No. 22171844.8.

Communication Pursuant to Article 94(3) EPC dated Dec. 18, 2023 for corresponding European Patent Application No. 22171844.8 (5 pages total).

European Examination Report dated Oct. 7, 2024 issued for European Divisional Application No. 22171844.8 (5 pages total).

* cited by examiner

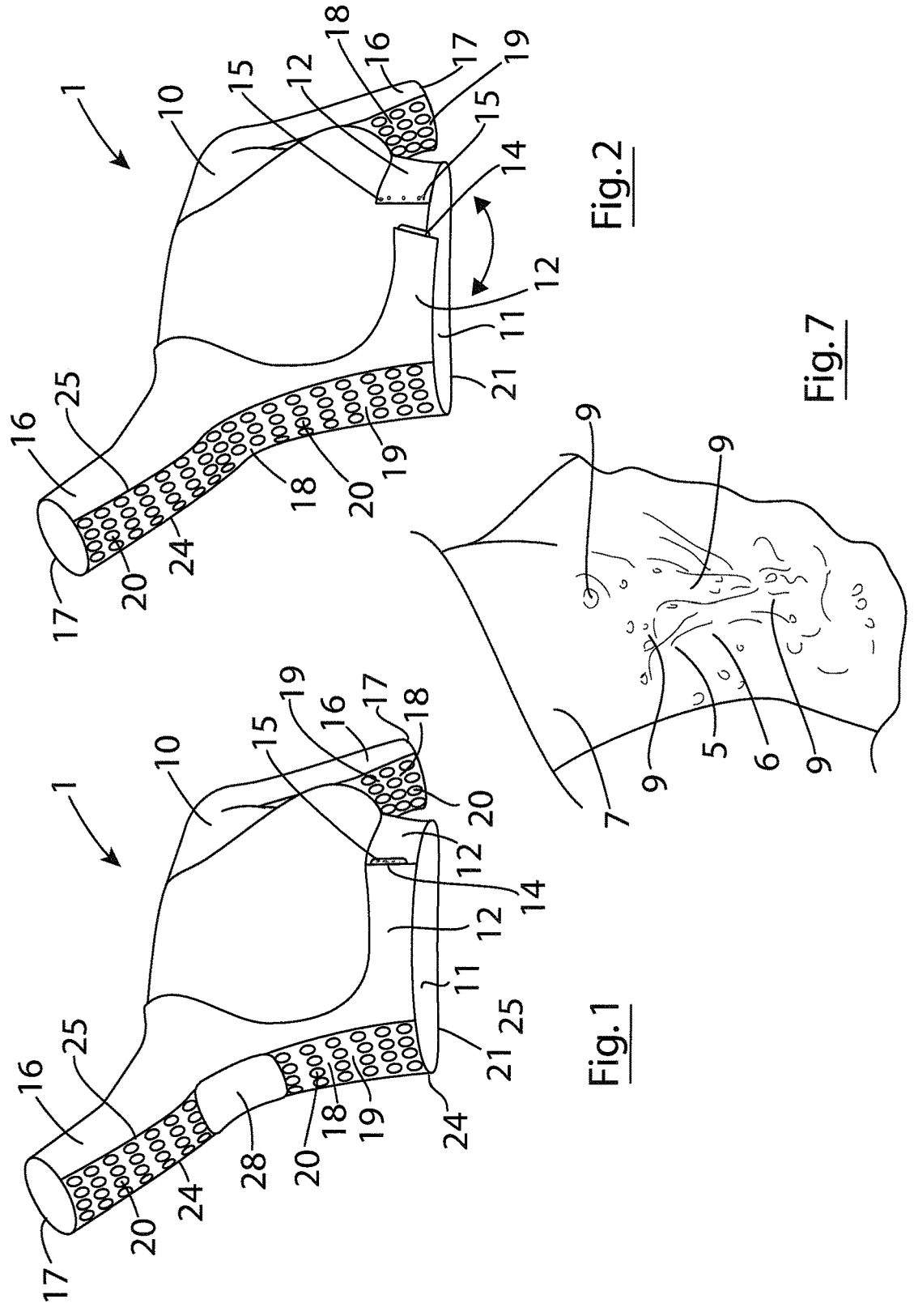
_Fig.1_
_Fig.2_
_Fig.7_

WOUND DRESSING

CLAIM OF PRIORITY

This application is a U.S. national stage filing under 35 U.S.C. § 371 of International Application No. PCT/EP2018/069842 filed Jul. 20, 2018 entitled "A WOUND DRESSING", which claims priority to Application No. IE S2017/0161, filed on Aug. 11, 2017, each of which is incorporated herein by reference in its entirety.

The present invention relates to a wound dressing device for securing a dressing in position on a wound of the body of a human or animal subject. The invention also relates to a method for retaining a dressing on a wound of the body of a human or animal subject.

When treating a wound, it is often advised to cover the wound with an absorbent dressing which both absorbs blood or other exudate, but also acts as a physical barrier against infection of the wound. Wounds and their surrounding area are however often sensitive and so wound care with dressings can irritate the wound and surrounding area, or indeed be painful.

For example, hidradenitis suppurativa is a recurring disease which affects many people, and results in sores (ie wounds) which require regular dressing. The sores which are associated with the disease tend to break out under the arm of a subject, for example, in the armpit of a subject, on the buttocks of a subject, on the inner thigh of a subject adjacent the crotch area. A particular problem of the disease is that the skin of an infected subject around the periphery of the affected area also becomes particularly sensitive, and prone to the spread of the sores. Accordingly, in general, it is not practicable to use pressure sensitive adhesive dressing, pressure sensitive tapes or other such pressure sensitive adhesive securing means for securing and retaining a dressing placed over the affected area. Any securing means with a pressure sensitive adhesive, such as an adhesive tape securing a dressing to an affected area, on coming into contact with the sensitive peripheral area would irritate the peripheral area, and cause pain, as well as adhesive allergy related sores. Thus, the only practical way of retaining a dressing placed over an affected area is to use a bandage. However, because of the locations in which the sores break out, in general, bandages are unsuitable for retaining a dressing placed over the affected area, particularly, in affected areas in the armpit of a subject, and the inner thigh adjacent the crotch area or indeed on the buttocks of a subject. Furthermore, even in more easily accessible areas, bandages while they may retain the dressing placed over an affected area, are inconvenient and time consuming to use, particularly since the dressings require relatively frequent changing, which depending on the subject may be as frequent as hourly, but, in general, would not be less than three to four times daily.

Similar difficulties arise when one tries to apply wound care to a burn or scald.

Accordingly, there is a need for a wound dressing device for retaining a dressing on a site to be treated of the body of a human or animal subject.

The present invention is directed towards providing such a device, and the invention is also directed towards providing a method for retaining a dressing on a wound to be treated of the body of a human or animal subject.

The inventor has surprisingly found that one can secure a dressing in the required position over a wound by the use of a retaining device and fastening element in association with the dressing, and without the need to present any rough or adhesive surface facing the wound.

Consequently, in a first aspect of the present invention, there is provided a wound dressing device for securing a dressing in position on a wound, wherein the wound dressing device comprises:

a. a retaining device for encompassing a portion of the body;

b. a dressing, and;

c. a fastening element that can secure the dressing in position;

the fastening element being configured at least substantially external to the retaining device, the dressing being configured at least substantially internal to the retaining device, such that the dressing can be secured to the fastening element through the retaining device.

The dressing can be secured to the fastening element through the retaining element in a variety of ways. For example, the dressing and the fastening element may be secured to each other by magnetic attraction. Alternatively, or additionally, the retaining device may comprise a perforated element defining at least one opening therethrough. The dressing and fastening element may therefore adhere together through the at least one opening.

The ability to secure the dressing in position on a wound comes from the fact that one can position and reposition the dressing in the interstices between the body and the retaining device until it is in position over the wound. Although, to a certain extent, the dressing may be retained in place by being braced between the wound and the encompassing retaining device, this position is secured more certainly by the securing of the dressing to the fastening element through the retaining device. Such a form of retention ensures that the dressing cannot move with respect to the retaining device, and as the retaining device is worn so as to encompass the portion of the body in which the wound is provided, the dressing is thereby secured in position on the wound. Without such a securing, the dressing may migrate from position, particularly during movement of the body, and most particularly when the dressing is placed over a wound at a joint, crotch or axilla (ie areas of considerably local movement).

In order to allow the repositioning of the dressing so as to be on the wound, and then to secure that position by being secured to the fastening element through the retaining device, the dressing and the fastening element should be capable of free-movement with respect to at least a portion of the retaining device that covers the wound. Consequently, if there is a connection to the retaining device, either or both of the dressing and fastening element may be connected via a flexible connection (eg one that permits movement in all directions of the dressing and/or fastening element with respect to the retaining device). In order to optimise the repositioning ability, the dressing, the fastening element, or both, are distinct structures from the retaining device.

The dressing may be fixedly secured or detachably secured in position, and so fixedly or detachably secured to the fixing element through the retaining device. The advantage of securing the dressing in a detachable manner is that it enables the user to position the dressing, secure it in place by securing the dressing to the fastening element through the retaining device, but if this is not positioned correctly, it can be detached from that secured position and re-secured in a more correct position.

The fastening element being configured when in use to be at least substantially external to the retaining device, the dressing being configured when in use to be at least substantially internal to the retaining device, such that the dressing can be secured to the fastening element through the retaining device. When not in use the dressing, fastening element and retaining element may be packaged for sale in any manner, eg separately, or the dressing and the fastening element may be packaged detachably bound together and separate from the retaining device.

The Retaining Device

The retaining device preforms its function by encompassing a portion of the body that includes the wound such that, in use, it defines the interstices between body and retaining device into which the dressing can be slipped.

There are therefore a number of forms that such a retaining device may take.

For example, when the wound dressing device is a wound dressing garment, the retaining device is for wearing as a garment that encompasses a portion of the body. The type of garment is dependent on where on the body the wound is to be found. In particular, the garment can be one that conforms to the body of the user of the dressing, ie a garment that is provided with elasticity such that after it is stretched for placement on the portion of the body to which it is designed to cover it hugs that portion of the body, thereby conforming to the shape of that portion of the body. For example, the garment may be a bodice, t-shirt, pants, leggings, sock, sleeve, hat, belt, bra, sports bra, crop-top, band, or any body—conforming garment. Particularly exemplified are wound dressing devices wherein the retaining device takes the form of a bodice or pants.

The retaining device may also be formed from bandages such as a tubular bandage, or a wrap bandage that can be wrapped around the portion of the body.

A tight fit around the body enhances the ability for the retaining device to retain the dressing in position. The tighter the fit, however, the more difficult it may become to position and reposition the dressing within the space between body and retaining device. Consequently, at least a portion of the retaining device may be elastic. Adequate movement of the bandage may be achieved when, for example, only a strip, running the length of the retaining device is elastic (for example, a strip running between apertures through which the portion of the body encompassed by the retaining device passes). Alternatively, the entire retaining device may be elastic. Consequently, a portion or all of the retaining device may be formed from an elastic material. The material may be stretchable in only one direction. The material may be stretchable in two directions (optionally perpendicular directions). The material may be stretchable in all directions. The elasticity may come from the material used to make the retaining device or that portion which is elastic. For example, the retaining device may be an elastic polymer and or, the material may be a woven fabric. For example, suitable materials are any of those conventionally used to make body hugging clothing, such as those made from cellulosic fibres, protein fibres, Lycra® (eg Spandex, elastane), or fabric blends.

Natural materials made from cellulosic fibres and suitable for use in the present invention include cotton and linen. Natural materials made from protein fibres and suitable for use in the present invention include silk or wool. Synthetic materials made from cellulosic fibres and suitable for use in the present invention include rayon (eg Lyocell/Tencell or Modal, Micro Modal blend, micro Tencel). Blended fabrics may also be used (including any blend of the foregoing).

As mentioned above, the retaining device may comprise a perforated element defining at least one opening therethrough. The perforated element may be formed as a mesh. Alternatively, the perforated element may form a sheet material wherein the perforations define openings through the sheet material (eg punched openings). In order to provide a superior level of retention, the retaining device can have a plurality of openings, for example, 2 or more, 3 or more, 4 or more, 5 or more, 10 or more, 20 or more, or 30 or more. As a consequence, the fastening element and the dressing can be configured to at least partially cover at least one opening (and optionally more than one opening, for example 2 or more, 3 or more, 4 or more, 5 or more, 10 or more, 20 or more, or 30 or more) in the perforated element, such that the dressing and the fastening element can adhere together through the at least one opening. The opening(s) therefore should be of a size that permits adhesion of dressing to fastening element. It is however beneficial if the opening(s) are not so large that the portion of the body that is to be encompassed by the wound dressing device may pass through or protrude through those openings. For example, each void defined by the opening could have an area of about 25 to 200 mm$^2$, 25 to 180 mm$^2$ or 60 to 180 mm$^2$. Each void could be separated by from 3 to 12 mm, 6 to 9 mm. For example, each void could be circular with diameter of 9 mm, each void separated by 6 mm. A plurality of openings can provide a larger area over which the dressing can be arranged to adhere to the fastening element, also providing more surface area for adherence of dressing to fastening element. Consequently, the sufficient numbers of openings may be provided so as to provide a perforated element that has at least 10%, 20%, 30%, 40%, 50%, 60%, 70%, 80%, 90%, 95%, or 98% of the perforate element by area being void. For example, the perforated element may have at least 10%, 20%, 30% or 40%. For example from 15% to 35% of the perforate element by area being void. These openings that extend through the perforated element can be arranged in a matrix.

The entire retaining device may be formed by the perforated element, thereby providing maximum flexibility for placement and securing of the dressing.

The perforated element may however instead only be provided in only a portion of the retaining device, eg the region on the retaining device that one knows will cover the wound, and optionally local area surrounding the wound. Consequently, when in use the perforated element is arranged so as to be provided adjacent to the wound. For example, wounds such as those exhibited by subjects suffering from hidradenitis suppurativa are commonly found on the inner thigh, the crotch, a portion of the arm and/or leg, the axilla, the torso or to one or both buttocks. Consequently, the perforated element may be arranged so as to be provided adjacent to the inner thigh, to the crotch, to a portion of the leg, to a portion of the arm, to a breast, to the waist or waist-line (ie the narrowest portion of the waist), to a foot, to the axilla, to the torso, and/or to one or both buttock, or to any part of the body affected by a wound of the subject wearing the device. When the retaining device is in the form of patents, the perforated element may extend over the crotch region and/or either one or both buttocks regions of the pants, possibly only over such regions. When the retaining device is in the form of a bodice, the perforated element may extend over the region of the axilla of the bodice, possibly only over such a region.

The retaining device may be seamless, or at least seamless over the portion covering the wound.

The Dressing

When the retaining device is provided without a perforated element, the dressing is provided entirely internal to the retaining device, when in use. Even when the wound dressing device includes a perforated element, the dressing may be entirely internal to the retaining device. It is possible for a portion of the dressing to extend through the openings in the perforated element, but only a minor portion of the dressing. It is required that the dressing remains substantially on the body side of the retaining device, such that it can be secured in place as described above. For example, less than 20, 10, 5, 2 or 1% of the dressing may be provided external to the retaining device.

The dressing may be provided in laminate form. In its simplest form, the dressing may comprise or consist of an absorbent pad and a surface that adheres to the surface of the fastening element. In the place of a surface that adheres to the surface of the fastening element, the dressing may include at least one magnet, or a ferromagnetic metal (or alloy thereof) that is attracted by a magnetic force (for example iron, nickel, cobalt, gadolinium, dysprosium and alloys such as steel) in order to enable attraction to the fastening element through the retaining device.

The absorbent pad may be made of any conventional material used to absorb blood and other wound exudate. Most conventionally, the absorbent pad is a gauze pad, optionally a cotton gauze pad, rayon gauze pad, cotton and rayon blend gauze pad, polyurethane pad, or mixtures thereof. The pad may be made of other materials or additionally include other materials, such as any one or more of gels, foams, hydrocolloids, alginates, hydrogels and polysaccharide pastes, granules and beads.

The most proximal layer (ie body-facing layer that is opposed to the surface that would adhere to the fastening element) may be a layer of, or film impregnated with, a therapeutically active agent (for example any one or more of an antibiotic agent, an anti-fungal agent, an anti-viral agent, clotting factors, and a wound-healing promoter). For example, the therapeutically active agent may be silver or alginate or mixtures thereof. The layer may also be impregnated with an odour reducing compound, such as charcoal. Such agents may additionally or alternatively be impregnated into any other layer of the dressing.

The layer of therapeutically active agent may be applied directly to a non-stick layer, which may be provided between the layer of therapeutically active agent and the absorbent pad. Alternatively, the non-stick layer may be provided as the most proximal (ie body-facing) layer of the dressing. As one of the features of this invention is that it is designed to locate itself over the wound without applying any potentially painful adhesive layer facing the wound, it is preferred that no such adhesive layer may be applied to the proximal side of the dressing.

The distal facing surface of the dressing may also have no adhesive layer, for example, simply being a distal surface of the absorbent pad. In such an instance the proximal surface of the fixing element must have an adhesive layer. However, the advantage of an adhesive layer being provided on the distal surface of the dressing is that it faces away from the wound and skin, and so does not require the proximal facing surface of the fixing element to be adhesive. The adhesive layer may be any form of layer that when in contact with the fixing element enables sticking together of the dressing to the fixing element. Consequently, the adhesive layer may be a glue, a gum, pressure sensitive adhesive, or a mechanical mechanism used to adhere two surfaces to one another, for example one or other of a material presenting hooks or eyes from the surface of that material (eg VELCRO®), or one part of a stud fastener (the corresponding part provided on the fixing element). When the adhesive layer is either of a material presenting hooks or eyes, it is the one that corresponds to that provided on the distal facing surface of the fastening element. It is preferred that the proximal surface of the dressing is a material presenting hooks, as it is preferred that such a rough-surfaced material is presented away from the wound and surrounding tender tissue.

Optionally, the adhesive layer is covered on its proximal side by an easy peel film, prior to use. This film being peeled away to reveal the adhesive layer during use.

Optionally the face of the dressing that is, in use, presented to the internal surface of the retaining element (ie the distal surface) is the same size and shape as the face of the fastening element that, in use, is presented to the external surface of the retaining device (ie the proximal surface), or more preferably is larger. This has the advantage of assisting to prevent any adhesive or rough surface of the fixing element from coming into contact with the skin or wound as when positioned correctly it would be shielded entirely from the body by the dressing.

The Fastening Element

The fastening element may comprise or most simply consist of the corresponding material that is attracted to or can adhere to that of the dressing. This is dependent on what is the nature of the surface of the dressing presented to the fastening element when in use. For example, (1) when the dressing includes a magnet, the fastening element may comprise or consist of a complementary magnet or ferromagnetic metal or its alloy, (2) when the dressing includes a ferromagnetic metal or its alloy, the fastening element may comprise or consist of a magnet, (3) when the proximal surface of the dressing includes an adhesive layer the fastening element may be a further adhesive layer or preferably a film to which the adhesive sticks (optionally an easy-peel film ie film to which the adhesive layer adheres but can easily be peeled away from). When the proximal surface of the dressing is a film (eg an easy-peel film), the fastening element may comprise or consist of an adhesive layer.

When the retaining device is provided without a perforated element, the fastening element is provided entirely external to the retaining device, when in use. Even when the wound dressing device includes a perforated element, the fastening element may be entirely external to the retaining device. It is possible for a portion of the fastening element to extend through the openings in the perforated element, but only a minor portion of the fastening element. It is required that the fastening element remains substantially on the distal side of the retaining device, such that it can secure the dressing in place as described above. For example, less than 20, 10, 5, 2 or 1% of the fastening element may be provided internal to the retaining device.

The wound dressing may include sensors embedded in any of the retaining device, the dressing or the fastening element. Sensors suitable for detecting a number of characteristics may be employed, for example temperature sensors, moisture sensors, pH sensors, bacterial sensors etc. When the sensors are provided in order to obtain data on the progress of healing of the wound, the sensors may be provided in the dressing. The sensors maybe provided on the surface of the dressing that in use faces the wound. The sensor may be equipped to provide feedback (ie in relation to the characteristic measured by the sensor, optionally quantitative feedback relating to that characteristic) to the subject wearing the device or to a health care provider responsible for the care of that subject. For example, when the sensor determines that the moisture level has reached a pre-determined level, it may be configured to alert the subject or their health care provider that the dressing needs changed. Such feedback can also be monitored by a health care provider in order to track the number and/or frequency of changes of dressing, and/or the improvement in the wound (eg. by a decrease in production of wound exudate as determined by a reduction in moisture sensed in subsequent dressings over a standard time-period). The feedback of information from sensor to subject or health care provider may be remote, eg by Bluetooth to a remote computer or mobile phone.

Wounds can usefully be treated by the application of heat or cold. Consequently, the wound dressing may include one or more hot or cold compress. This compress may be incorporated into a pocket provided in any of the retaining device, the dressing or the fastening element. The compress is preferably positioned such that in use it is close to the wound (ie sufficiently close so that the heat or cold is transmitted directly to the wound). The compress may therefore be incorporated into the dressing.

As the wound dressing device may be provided with the dressing and fastening element releasably adhered together, a further aspect of the present invention is a combined dressing and fastening element, wherein one face of the dressing adheres to a corresponding face of the fastening element. All features of the dressing and fastening element described above may be applied to this further aspect of the present invention. For example, the face of the dressing being the same size and shape as the face of the fastening element, or preferably larger. When the dressing is larger than the fastening element, the dressing may shield the wound from any adhesive layer.

In a further aspect of the present invention, there is provided a method for applying the wound dressing device as described above to the body, the method comprising the steps of:

a. placing the dressing on a wound;

b. placing a retaining device on the body so as to encompass the portion of the body where the wound is located;

c. placing a fastening element over the portion of the retaining device that covers the dressing, thereby securing the dressing in place over the wound.

When the retaining device comprises a perforated element, step b. includes the positioning of the perforated element of the retaining device over the wound, and step c. includes placing the fastening element over the portion of the perforated element that covers the dressing, thereby securing the dressing in place over the wound. This thereby secures the dressing to the retaining device located over the wound. Step a. may be performed before step b. Alternatively, step b. may be performed before step a. In this latter order, the dressing is slipped into the interstices formed between body and retaining device.

The method may also include re-positioning of the dressing and re-securing it by placing the fastening element, for example, over the portion of the perforated element that covers the dressing. This enables the user to re-position the dressing if it is not in optimum position without having to remove the retaining device.

The wound dressing may be applied to any animal body, for example a human body. The wound dressing may however be used in the context of veterinary medicine and so can be applied to a non-human animal, such as companion animals (eg cats, dogs etc) or livestock (such as cows, sheep, goats etc).

The skilled person would understand what is meant by a wound. For example, a wound maybe any injury resulting in damage to the skin of the body. For example, this can be from a cut or a blow or from a scald or a burn. Wounds may also be caused by disease, as is the case with wounds caused by hidradenitis suppurativa.

Figures 4, 5, 6:
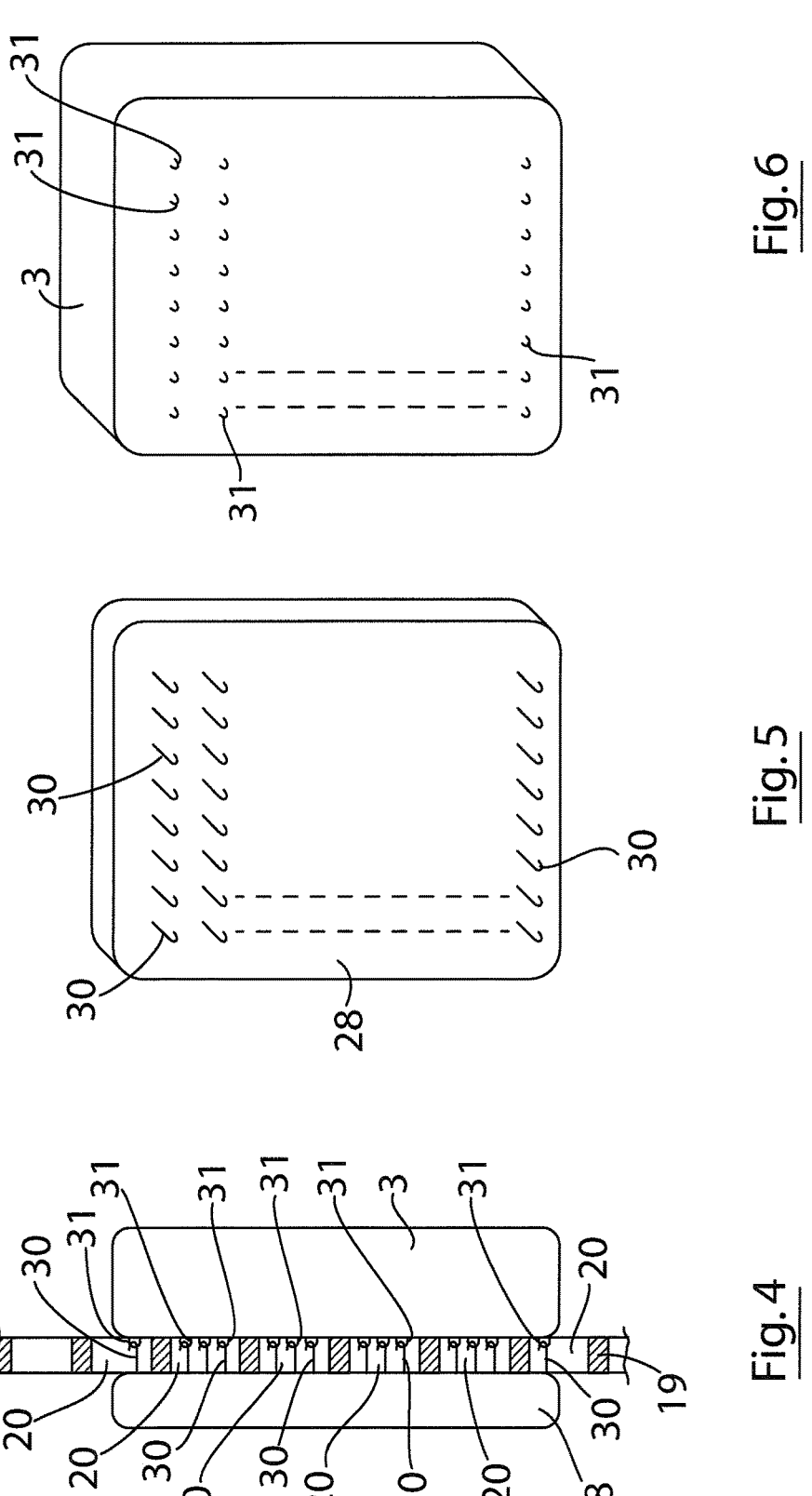

The invention will be more clearly understood from the following description of some embodiments thereof, which are given by way of example only, with reference to the accompanying drawings, in which:

FIG. 1 is a perspective view of a retaining device according to the invention in use retaining a dressing on a site to be treated of the body of a human or animal of a subject, FIG. 2 is a perspective view of a portion of the retaining device of FIG. 1, FIG. 3 is another perspective view of the portion of FIG. 2 of the retaining device of FIG. 1, FIG. 4 is an enlarged cross-sectional side elevational view of a portion of the retaining device of FIG. 1, FIG. 5 is a perspective view of another portion of the retaining device of FIG. 1, FIG. 6 is a perspective view of a dressing for the retaining device of FIG. 1, FIG. 7 is a perspective view of the underarm of a subject suffering from Hidradenitis suppurativa, and FIG. 8 is a perspective view of a portion of a retaining device according to another embodiment of the invention.

Figure 9:
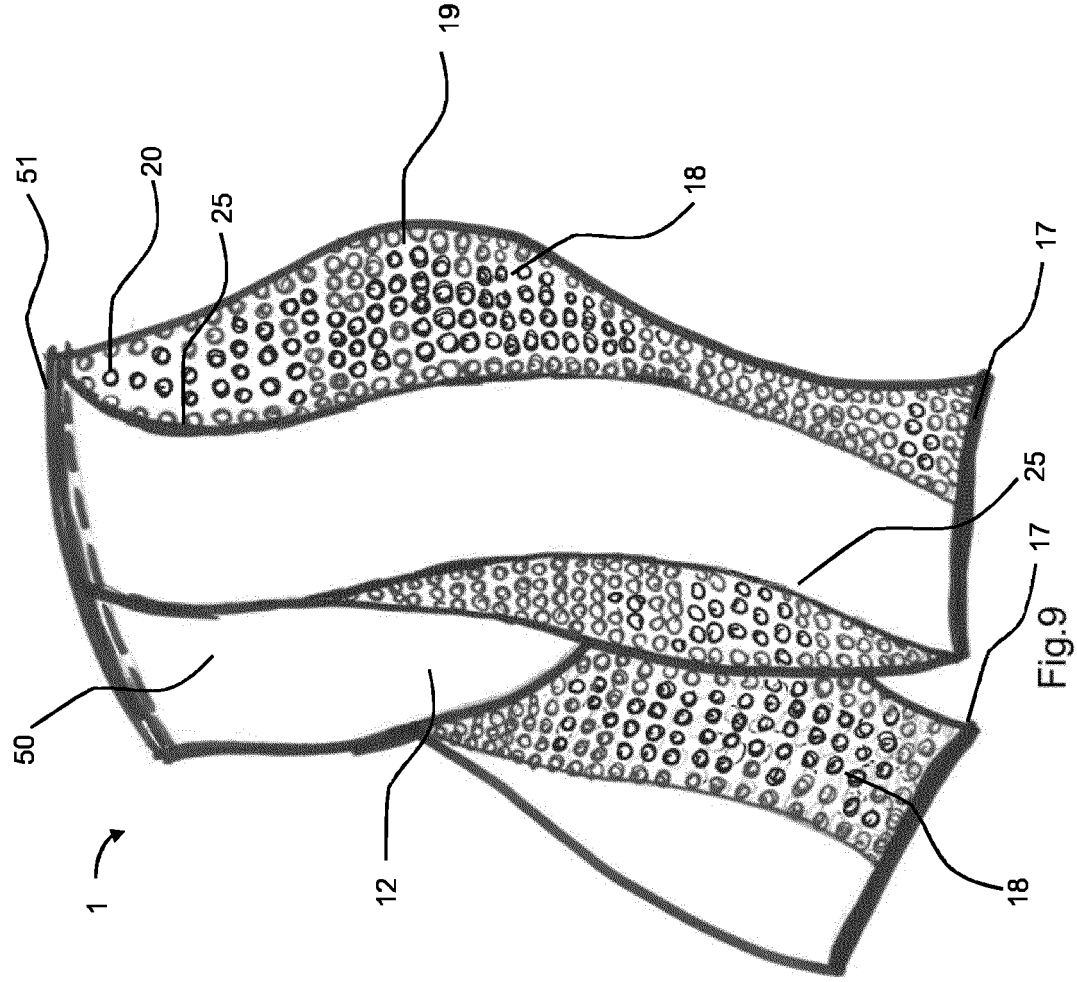

FIG. 9 is a perspective view of a further embodiment of the present invention, presented in the form of pants.

Referring to the drawings and initially to FIGS. 1 to 5 thereof, there is illustrated a retaining device according to the invention indicated generally by the reference numeral 1 for retaining a dressing 3 to a site, in this embodiment of the invention a site 5 in an armpit 6 under an arm 7 of a subject. The site 5 comprises sores 9 which have broken through the skin at the site 5 in the armpit 6. The dressing 3 is to be applied to the site 5 in order to treat the sores 9.

The retaining device 1 according to the invention comprises a garment, which in this embodiment of the invention is provided by a bodice type garment 10. The garment 10 comprises a back portion 11 and a pair of front portions 12 extending from the back portion 11 on either side thereof and configured to be joined together beneath the breasts of a subject. One of the front portions 12 terminates in hooks 14 which are configured to engage corresponding eyes 15 in the other front portion 12 for securing the garment to the subject around the torso. A pair of short sleeves 16 terminating at distal ends 17 extend from the garment 10. A pair of perforated elements 18 are provided on each side of the garment 10 between the back portion 11 and the respective front portions 12. Each perforated element 18 comprises a perforated sheet 20 of fabric or textile material comprising a plurality of openings 20 extending therethrough, which in this particular embodiment of the invention are arranged in a matrix four across. Each perforated sheet 19 extends from the lower end 21 of the garment 10 on each side thereof upwardly and terminates in the distal end 17 of the corresponding sleeve 16. The perforated sheets 19 are secured to the back portion 11 of the garment 10 and to the back portion of the corresponding sleeves 16, by seams 24, and are secured to the corresponding front portions 12 of the garment 10, and to the front portion of the corresponding sleeves 16 by seams 25.

A fastening element, which in this embodiment of the invention comprises a fastening pad 28 is provided for securing the dressing 3 to the corresponding perforated sheet 19 with the perforated sheet 19 sandwiched between the dressing 3 and the fastening pad 28 with the dressing 3 located adjacent the site 5 with the dressing 3 placed over the sores 9 for treating thereof. The fastening pad 28 in this embodiment of the invention comprises a pad of fabric or textile material, which is of area substantially similar to the area of the dressing 3. A fastening means, in this embodiment of the invention hooks and eyes of the type sold under the trademark VELCRO are provided for securing the dressing 3 to the fastening pad 28 through the openings 20 in the corresponding perforated sheet 19. In this embodiment of the invention hooks 30 of the hooks and eyes extend from the fastening pad 28 and engage eyes 31 extending from the dressing 3 through the openings 20 in the perforated sheet 19. Thus, the garment 10 acts as a securing means for securing the corresponding perforated sheet 19 adjacent the site 5, and in turn, for securing the dressing 3 abutting the site 5 when the dressing 3 is secured to the perforated sheet 19 by the fastening pad 28.

The fabric or textile material of the back portion 11 and the front portions 12 of the garment 10 may be any suitable material. However, it is believed that a suitable material would be stretch hypoallergenic cotton. A suitable material for the perforated sheets 19 would be perforated hypoallergenic silk fabric or indeed any other suitable fabric, which preferably, would be hypoallergenic. The material of the fastening pad may also be any suitable material, such as a textile or fabric material, but desirably, would also be a hypoallergenic material, for example, hypoallergenic silk or cotton.

In use, typically, the garment 10 is placed on the subject with the arms of the subject extending through the sleeves 17. The front portions 12 are secured together by securing the hooks 14 and the eyes 15. The dressing is then placed in the affected armpit 6 over the sores 9 at the site 5. The fastening pad 28 is then secured to the dressing 3 with the hooks 30 extending from the fastening pad 28 through the openings 20 in the corresponding perforated sheet 19 engaging the eyes 31 of the dressing 3. With the dressing 3 secured to the corresponding perforated sheet 19 by the fastening pad 28, with the perforated sheet 19 sandwiched between the dressing 3 and the fastening pad 28, the dressing 3 is thereby securely retained in place on the perforated sheet 19, and in turn the dressing 3 is retained adjacent the site 5 and placed over the sores 9 by the garment 10.

Referring now to FIG. 8 there is illustrated a garment indicated generally by the reference numeral 40 of a retaining device according to another embodiment of the invention. The garment 40 is substantially similar to the garment 10 of the retaining device 1, and similar components are identified by the same reference numeral. The main difference between the garment 40 and the garment 10 of the retaining device 1 is in the perforated sheets 42. In this embodiment of the invention the perforated sheets 42 comprise a mesh material. Openings 43 through the perforated sheets 42 are formed by interstices of the mesh material. Additionally, in this embodiment of the invention the perforated sheets 42 do not extend from the lower end 21 of the garment 40 to the distal end 17 of the corresponding sleeve 16, rather, the perforated sheets 42 are located in corresponding openings 45 formed in the garment 40 adjacent the opposite sides thereof, and extending into the under part of the corresponding sleeve 16.

Otherwise, the garment 40 and the remainder of the retaining device according to this embodiment of the invention is similar to the retaining device 1. A fastening pad similar to the fastening pad 28 with hooks 30 extending therefrom is provided for engaging corresponding eyes of a dressing similar to the dressing 3 described with reference to the retaining device 1 for securing the dressing to the corresponding perforated sheet 42 with the dressing located on the perforated sheet 42, so that when the garment 40 is worn the dressing is located adjacent the site extending over the sores 9 in the armpit of the subject.

Accordingly, the use of the garment 40 is similar to that of the garment 10 of the retaining device 1.

While the fastening means for securing the fastening pad to the dressing with the corresponding perforated sheet 19 sandwiched between the dressing 3 and the fastening pad 28 has been described as comprising hooks and eyes of the type sold under the trademark VELCRO (where VELCRO is mentioned throughout this application, it should be understood to mean VELCRO or any other hook and loop mechanical arrangement capable of adhering to each other), any other suitable fastening means may be provided. For example, in some embodiments of the invention it is envisaged that either the fastening pad or the dressing would be provided with a pressure adhesive which would bond the dressing to the fastening pad through the opening in the corresponding perforated sheet 19, and in which case, it is envisaged that the adhesive would be a pressure adhesive, and typically, would be provided on the dressing.

Additionally, it will be appreciated that any other suitable material or materials may be used for the garment, the perforated elements and the fastening pad. Indeed, it is envisaged in certain cases, that the perforated element may be provided with a single opening only, and the fastening pad would be secured to the dressing through the single opening, with the remainder of the perforated element sandwiched between peripheral portions extending around the dressing and the fastening pad. It is also envisaged that in certain cases, the garment may be formed entirely by the perforated sheet material of the perforated element.

It will be appreciated that the fastening pad may be re-useable or disposable, and in cases where the fastening pad is re-useable, the fastening pad would be of a suitable washable material, for example, a soft silicone strip type material. Needless to say, any other suitable fastening element may be provided.

While the securing means has been described as comprising a garment, any other suitable securing means may be provided, and the form of the securing means will largely be dictated by the location of the site on the body of the subject which is to be treated with the dressing. For example, in cases where the site is on a relatively easily accessible portion of a leg or an arm of a subject, or indeed, on the neck of a subject, the garment may be provided in the form of a sleeve. The sleeve typically would be of an expandable and preferably, breathable fabric or textile material. In the case of a site to be treated on the neck of a subject, the sleeve may be split longitudinally to facilitate securing around the neck, and the two free edges of the sleeve could be secured by hooks and eyes, stud fastener, or hooks and eyes of the type sold under the trademark VELCRO.

It is also envisaged that in the case of an easily accessible site on the torso of a subject, the securing means may also be provided in the form of a sleeve. Indeed, it will be readily apparent to those skilled in the art that the sleeves in each case may be formed entirely by the perforated sheet material of the perforated element, or may be formed by a material different to the perforated element, with the perforated element located to facilitate securing the dressing to the perforated element with the fastening pad, so that the perforated element with the dressing secured thereto by the fastening pad will be located over the site to be treated when the sleeve of the securing means is secured around the torso of the subject.

Needless to say, in the cases where the site is on the inner upper portion of the thigh of a subject adjacent the crotch, the garment may be provided in the form of pants, for example, in the form of shorts.

Referring now to FIG. 9, there is illustrated a garment indicated generally the reference numeral 50 of a retaining device 1 according to another embodiment of the invention. The garment 50 is for the lower body but similar components to upper body garments 10 and 40 are identified with the same reference numeral. The garment 50 comprises a front fabric portion 12 which is connected to perforated elements 18 by seams 25. The perforated element 18 comprises a perforated sheet 19 which extends from the proximal end 51 to the distal end 17 of garment 50. The perforated element 18 comprises a plurality of openings 20.

It will also be appreciated that in certain cases, when the retaining device is provided in the form of a bodice, that the retaining device may be provided with one sleeve only which would be provided for retaining the dressing adjacent the site in the armpit of the subject. It is also envisaged that in cases where the retaining device is provided in the form of shorts or pants, the shorts/pants could be provided with one sleeve only for retaining the dressing adjacent an affected site at the upper portion of the thigh of a subject.

The invention is not limited to the embodiments hereinbefore described which may be varied in construction and detail.

The invention claimed is:

1. A wound dressing device for securing a dressing in position on a wound, wherein the wound dressing device comprises:
   a. a retaining device for encompassing a portion of a body;
   b. a dressing; and
   c. a fastening element configured to secure the dressing in position;
   wherein a majority of the fastening element is external to the retaining device and a majority of the dressing is internal to the retaining device relative to the body,
   wherein the dressing is configured to be attached directly to the fastening element through the retaining device such that the retaining device is interposed between fastening element and the dressing,
   wherein the dressing is configured to be attached directly to the fastening element based on:
      the retaining device comprising a perforated element defining a plurality of openings therethrough, thereby permitting the fastening element and the dressing to at least partially cover the plurality of openings in the perforated element such that the dressing and the fastening element attach together through the plurality of openings such that the dressing can be secured to the fastening element through the retaining device, wherein the plurality of openings are solely formed by the retaining device, and
   wherein the dressing is configured to be re-positioned on a wound relative to the retaining device.

2. The wound dressing device as claimed in claim 1, wherein the wound dressing device is a wound dressing garment, and wherein the retaining device is configured to be worn as a garment that encompasses a portion of the body.

3. The wound dressing device as claimed in claim 2, wherein the garment is a bodice, t-shirt, pants, trousers, sock, sleeve, hat, belt, stocking, bra, sports bra, crop-top, band, or any body-conforming garment.

4. The wound dressing device as claimed in claim 1, wherein the perforated element is formed from a mesh or a fabric with a plurality of holes.

5. The wound dressing device as claimed in claim 4, wherein the holes extending through the perforated element are arranged in a matrix.

6. The wound dressing device as claimed in claim 1, wherein the retaining device is a tubular bandage comprising a perforated element defining at least one opening therethrough.

7. The wound dressing device as claimed in claim 1, wherein at least a portion of the retaining device is formed from an elastic fabric.

8. The wound dressing device as claimed in claim 1, wherein at least one of 10%, 20%, 30%, 40%, 50%, 60%, 70%, 80%, 90%, or 95% of the perforated element is void.

9. The wound dressing device as claimed in claim 1, wherein, in use, the perforated element is arranged so as to be provided adjacent to the wound.

10. The wound dressing device as claimed in claim 1, wherein, in use, the perforated element is arranged so as to be provided adjacent to an inner thigh, to a crotch, to a portion of a leg, to a portion of an arm, to a breast, to a waist-line or waist, to a foot, to an axilla, to a torso, to one or both buttocks, or to any part of the body affected by a wound of a subject wearing the retaining device.

11. The wound dressing device as claimed in claim 1, wherein the perforated element forms a portion of the retaining device.

12. The wound dressing device as claimed in claim 1, wherein, when in use, the dressing is provided entirely internal to the retaining device.

13. The wound dressing device as claimed in claim 1, wherein a face of the dressing that is, when in use, presented to an internal surface of the retaining device is a same size and shape as a face of the fastening element that, when in use, is presented to an external surface of the retaining device.

14. The wound dressing device as claimed in claim 1, wherein the dressing comprises an absorbent pad and a surface that adheres to a surface of the fastening element.

15. The wound dressing device as claimed in claim 1, wherein the dressing and the fastening element are adapted to adhere to each other by virtue of an adhesive layer being applied to a face of either or both of the dressing or the fastening element.

16. The wound dressing device as claimed in claim 1, wherein the dressing and the fastening element are adapted to adhere to each other by virtue of one of hooks or eyes extending from the fastening element and the other one of hooks and eyes extending from a surface of the dressing.

17. The wound dressing device as claimed in claim 1, wherein, when in use, the fastening element is entirely external to the retaining device.

18. The wound dressing device as claimed in claim 1, wherein the retaining device, the dressing and the fastening element are discrete structures.

19. The wound dressing device as claimed in claim 1, wherein the dressing is an absorbent pad which absorbs blood or other exudate.

20. The wound dressing device as claimed in claim 1, wherein the retaining device is configured to retain a dressing on a site to be treated of the body of a human or animal subject.

21. The wound dressing device as claimed in claim 1, wherein the fastening element is not configured to attach to the retaining device.

* * * * *